United States Patent [19]
Klardie et al.

[11] Patent Number: 5,996,779
[45] Date of Patent: Dec. 7, 1999

[54] DENTAL IMPLANT PACKAGE

[75] Inventors: Michael Robert Klardie, Bloomington; Jeremy Matthew Huotari, Mound; Jean B. Christensen, Minneapolis; Peter Bjork Swenson, Eden Prairie, all of Minn.

[73] Assignee: Lifecore Biomedical, Inc., Chaska, Minn.

[21] Appl. No.: 09/099,698

[22] Filed: Jun. 19, 1998

[51] Int. Cl.⁶ .................................................. A61B 19/02
[52] U.S. Cl. .......................... 206/63.5; 433/174; 215/350; 220/831; 220/844
[58] Field of Search .................................. 206/63.5, 368, 206/369, 339; 433/173, 174, 201.1; 215/350, 235; 220/843, 844, 831, 671, 737, 739, 921

[56] References Cited

U.S. PATENT DOCUMENTS

| | | |
|---|---|---|
| 3,462,034 | 8/1969 | Friedberg ................................. 215/350 |
| 4,712,681 | 12/1987 | Branemark et al. . |
| 4,763,788 | 8/1988 | Jorneus et al. . |
| 4,809,874 | 3/1989 | Pehr ........................................ 220/338 |
| 4,934,556 | 6/1990 | Kleissendorf ........................... 220/269 |
| 5,062,800 | 11/1991 | Niznick . |
| 5,368,160 | 11/1994 | Leuschen et al. . |
| 5,538,428 | 7/1996 | Staubli .................................... 433/173 |
| 5,582,299 | 12/1996 | Lazzara et al. . |
| 5,622,500 | 4/1997 | Niznick .................................. 433/173 |
| 5,755,575 | 5/1998 | Biggs et al. . |

OTHER PUBLICATIONS

Derwent Abstract of SE 8406591; WPI Acc. No. 86–223652/34.

"A new twist on reducing chair time . . . ", Spline Twist MP–1, SulzerMedica Sulzer Calcitek, Inc., brochure, Rev. Sep. 1998.

*Primary Examiner*—Paul T. Sewell
*Assistant Examiner*—Nhan T. Lam
*Attorney, Agent, or Firm*—Vidas, Arrett & Steinkraus

[57] ABSTRACT

A dental implant package for supplying a dental implant and healing screw without impacting the sterility thereof is disclosed. The package comprises an elongated tubular housing with an open first end and a closed second end for receiving the dental implant and a cap for closing the tubular housing. The cap has a retainer therein for holding a healing screw and is constructed and arranged so that the cap in the fully open position presents the healing screw and dental implant side-by-side.

36 Claims, 3 Drawing Sheets

DENTAL IMPLANT PACKAGE

BACKGROUND OF THE INVENTION

This invention relates to a sterilizable packaging for transporting dental implants and related components.

The use of dental implants is commonplace in the practice of dentistry. To minimize the risk of infection, it is necessary to sterilize an implant prior to placement. To avoid the need to sterilize implants in the dental office, a number of manufacturers now provide sterilized implants to the practitioner. In an effort to deliver these sterile dental implants to dentists a number of dental implant packages have been developed.

It is important when packaging a dental implant, that the implant be readily accessible and provided in a convenient presentation to the dentist. If the implant is not easily accessible, the dentist may compromise the sterility of the implant in an attempt to access it. The need for a convenient packaging becomes more acute where multiple components such as an implant and a healing screw are involved. Optimally, both components will be readily accessible to the dentist.

A number of dental implant packages have been developed. U.S. Pat. No. 4,763,788 to Jörnéus et al. discloses a hermetically sealed glass capsule enclosing an dental implant. The dental implant rests with an inner sleeve which is held in place in the capsule by a spring. The implant can only be accessed by breaking the glass capsule.

U.S. Pat. No. 5,062,800 to Niznick discloses a dental implant package including a two-part handle that can be attached to the implant inside of the package.

U.S. Pat. No. 5,582,299 to Lazzara et al. discloses a dental implant package in which, in one embodiment, a dental implant and a related component are presented side by side. In an alternate embodiment, a dental implant compartment is provided with a cover which includes a compartment for the related component. In this alternate embodiment, however, the implant and related component are not presented side by side.

There is a need for sterilizable dental implant package structures which, when opened, present the implant and a healing screw in an accessible side-by-side relationship.

SUMMARY OF THE INVENTION

The present invention is directed to a dental implant package for supplying a dental implant and healing screw side-by-side to a dental practitioner in a field. The package comprises an elongated tubular housing for receiving at least a portion of the dental implant. The housing has an open first end and a closed second end and the length of the elongated tubular housing exceeds that of the dental implant. The package further comprises a cap closing the first end of the elongated tubular housing. The cap is attached to the first end of the housing via a connector configured so that when the package is opened, the healing screw is presented to the practitioner side-by-side with the dental implant. The cap and elongated tubular housing further are constructed and arranged so that the healing screw and dental implant are enclosed within the package when the cap is closed. The cap also comprises a retainer for the healing screw. Optionally, the package may further comprise a removable inner sleeve resting within the elongated tubular housing and enclosing at least a part of the dental implant when the implant is present in the package.

The present invention is also directed to a closed, sterilized dental implant package comprising an elongated capsule having a first end with an opening therein and a second end which is closed. The elongated capsule receives at least a portion of the dental implant. The package also includes a cap for closing the first end of the capsule. The cap is connected to the elongated capsule by a connector. Together the cap and the elongated capsule encompass the dental implant and healing screw. The cap is constructed and arranged to present the healing screw alongside the implant when the cap is fully opened. The cap further comprises a retainer for the healing screw. The package optionally comprises a removable inner sleeve for holding the dental implant. The removable inner liner rests in the elongated capsule and is supported by one or more optional sleeve stop surfaces therein. Finally, an optional base extends from the second end of the elongated capsule.

The present invention is also directed to an inventive package in combination with a dental implant and a healing screw and optionally closed and sterilized.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
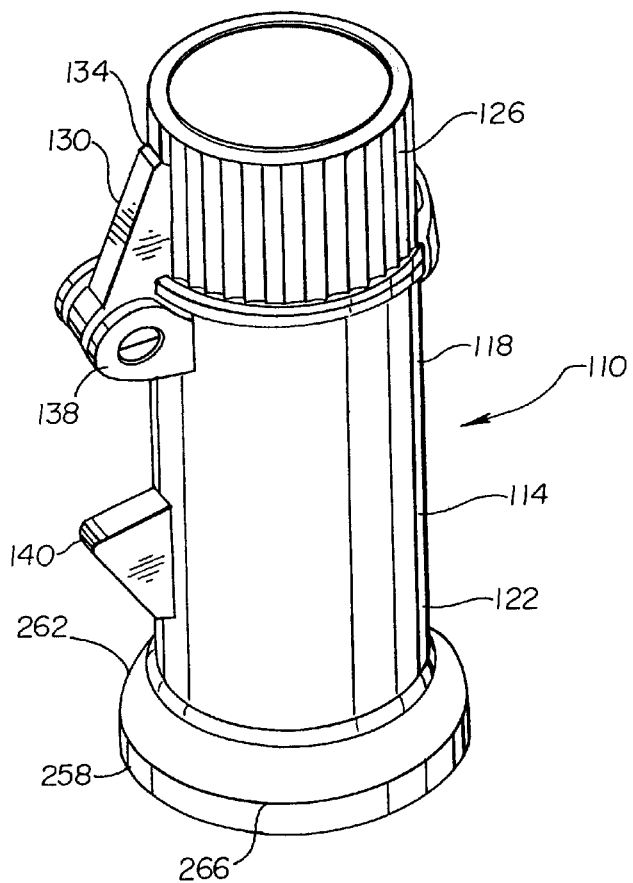
FIG. 1 shows a perspective view of the inventive dental implant package.
Figure 2:
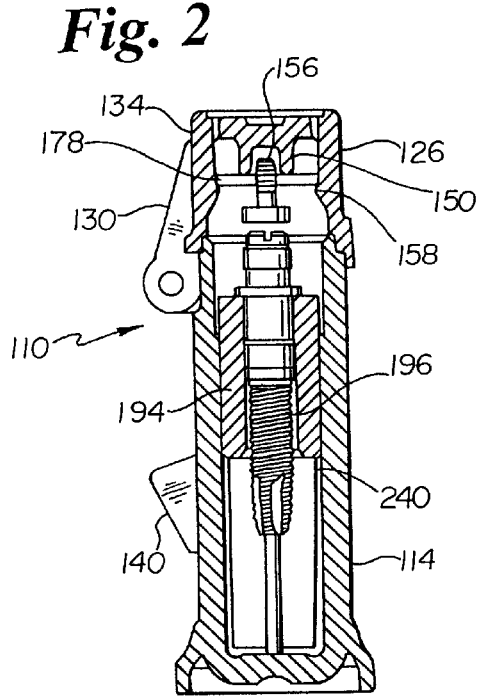
FIG. 2 shows a side elevational cut-away view of the dental implant package.
Figure 3:
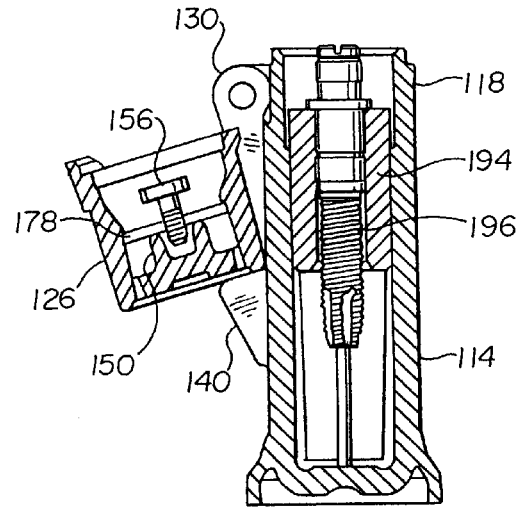
FIG. 3 shows a side elevational cut-away view of the dental implant package of FIG. 2, with the cap fully opened.

As shown in FIGS. 1–3, the inventive dental implant package, shown generally at 110, comprises an elongated tubular housing 114 having an open first end 118 and a closed second end 122. The elongated tubular housing has a length longer than the dental implant and is intended for receiving at least a portion of the dental implant.

Closing the first end 118 of tubular housing 114 is a cap 126 which, when removed from end 118 provides access to the implant located in elongated tubular housing 114. As shown in FIGS. 1–3, cap 126 is attached via a first hinge element 130 extending from exterior surface 134 of cap 126 and a second hinge element 138 extending from first end 118 of tubular housing 114. First hinge element 130 and second hinge element 138 cooperate so as to allow housing 114 to be opened at first end 118. Cap 126, elongated tubular housing 114 and hinge elements 130 and 138 are constructed and arranged so as to present a healing screw in a manner which allows for side-by-side access with a dental implant when cap 126 is removed from end 118 as shown in FIG. 3 and further to enclose the healing screw and dental implant within the dental implant package when cap 126 is on end 118, as shown in FIG. 2. Emanating from tubular housing 114 is a support surface 140 which is designed to provide support to cap 126 when healing screw 156 and dental implant 196 are presented side-by-side and pressure is applied to the cap, such as when a healing screw is removed therefrom.

Although cap 126 is shown attached to elongated housing 114 via a hinge structure, other forms of attachment are possible, for instance, a ball and socket joint or a flexible strip that is connected at one end to the cap and at the other end to the elongated housing.

Figure 4:
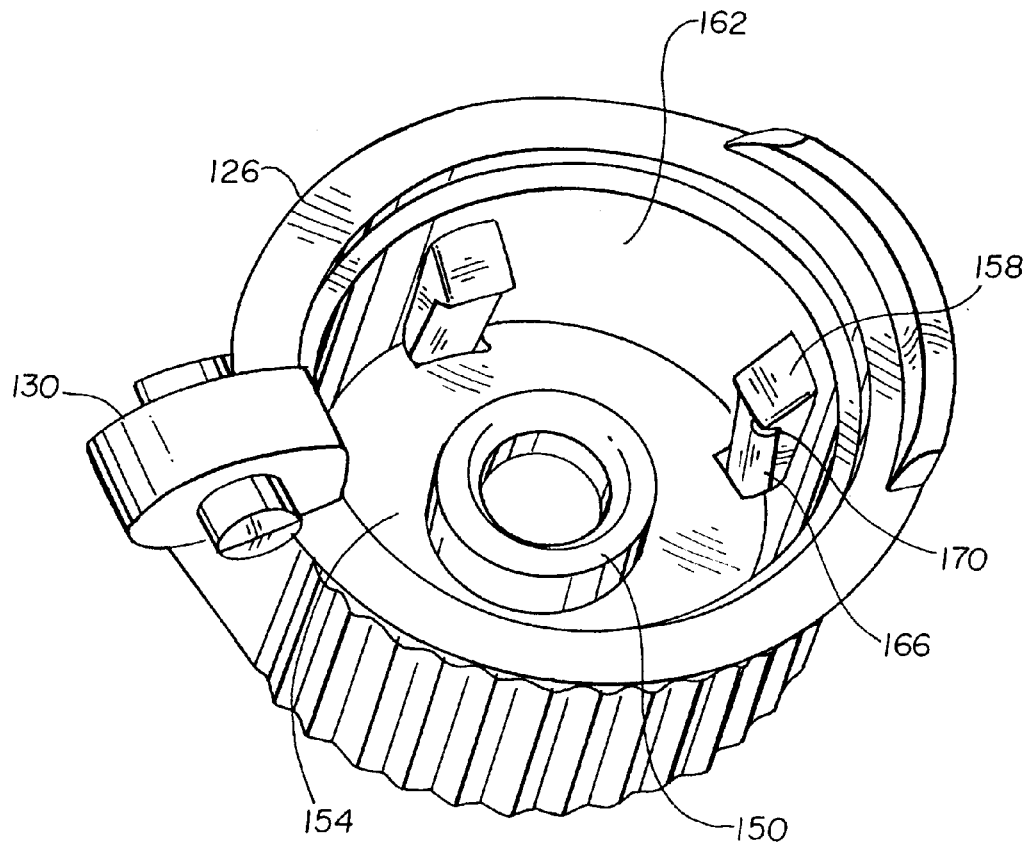
FIG. 4 shows a perspective view of the cap.
Figure 5:
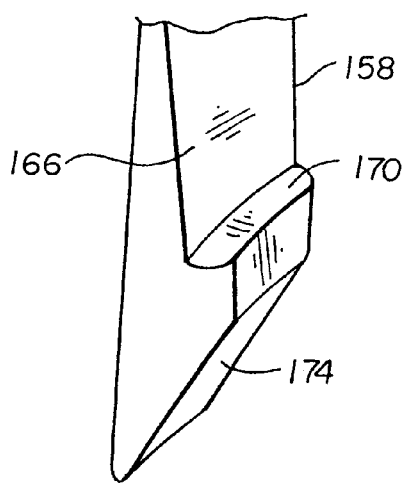
FIG. 5 shows a perspective view of a retainer stop surface in the cap.
Figure 6:
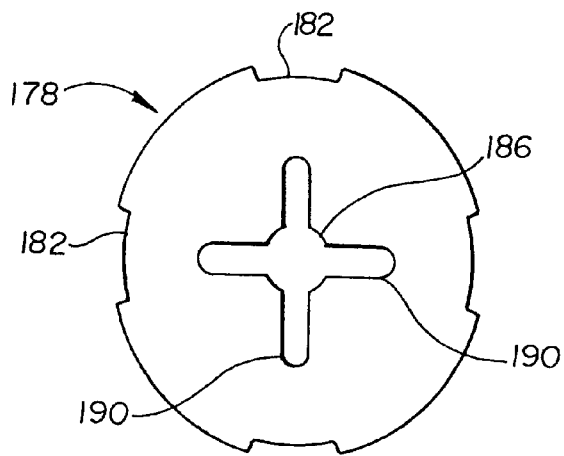
FIG. 6 shows a top view of the retainer in the cap.

Cap 126, as shown in FIG. 4, has a tubular section 150 emanating from the top 154 of the cap supporting a retainer 178 and holding at least a portion of healing screw 156. Four retainer stop surfaces 158 (two of which are shown, the remaining two situated opposite the two that are shown) emanate from the inner surface 162 of the cap. Retainer stop surfaces 158, as shown in FIG. 5, have a downward sloping first section 166, a shelf section 170 which is parallel to top 154 of cap 126 and a downward sloping second section 174. Shelf section 170 serves to hold a retainer shown generally at 178 in FIG. 6. While four retainer stop surfaces are depicted, the cap may have additional or fewer retainer stop surfaces.

Retainer 178 is substantially disk shaped and holds healing screw 156. Retainer 178 has a perimeter with notches 182 cut therein so as to cooperate with retainer stop surfaces 158 on the inner surface 162 of cap 126. For each retainer stop surface 158 there is a corresponding notch 182. Retainer 178 is held within cap 126 between tubular section 150 and shelf section 170 and further has a through-hole 186 through the center into which the healing screw is inserted. The diameter of through-hole 186 is such that the healing screw fits snugly therein. Retainer 178 has two perpendicular slots 190 extending through the center of the retainer to grip the healing screw. In other embodiments, more slots may be used. Retainer 178 is also arranged such that a bottom surface of the healing screw retained therein rests against the top 154 of cap 126 but within tubular section 150.

Figure 7:
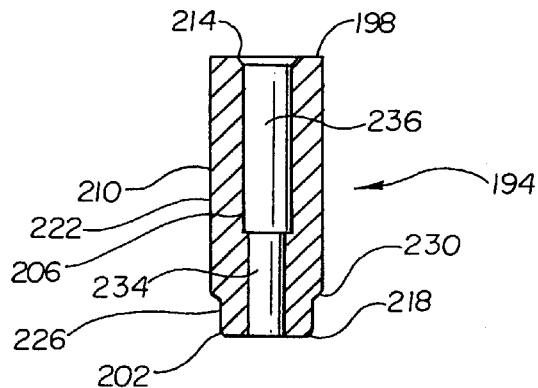
FIG. 7 shows a side elevational view of the removable inner sleeve in cross-section.

Dental implant package 110 may be provided with an optional removable inner sleeve, shown generally at 194 in FIG. 7, which rests within elongated housing 114. Inner sleeve 194 is coaxial with tubular housing 114 and encloses at least a part of dental implant 196 when the implant is present in the package. Inner sleeve 194 has an annular top 198, an annular bottom 202, an inner surface 206 extending between annular top 198 and annular bottom 202 and an outer surface 210 extending between annular top 198 and annular bottom 202. A portion 214 of annular top 198 is optionally chamfered inward toward inner surface 206. Similarly, a portion 218 of annular bottom 202 is optionally chamfered toward outer surface 210 and a portion of annular bottom 202 may also be optionally chamfered inward toward inner surface 206.

The inner sleeve may have a constant outer diameter or may have one or more regions of differing diameter. The inner sleeve, as shown in FIG. 7 has an upper outer region 222 having a uniform first outer diameter and a lower outer region 226 having a uniform second outer diameter smaller than the first outer diameter. An optional chamfered outer transition region 230 extends between upper outer region 222 and lower outer region 226. Although chamfered outer transition region 230 is shown with a chamfer angle of about 45° relative to a horizontal reference plane, chamfer angles in a range of about 45° to about 90° are contemplated as well.

Further, inner sleeve 194 may have a constant inner diameter along the length of the sleeve or may have one or more regions of differing diameter. As shown in FIG. 7, inner sleeve 194 has an upper inner region 236 having a uniform first inner diameter and a lower inner region 234 having a uniform second inner diameter, the second inner diameter smaller than the first inner diameter. Although the inner diameter of the sleeve is shown as stepped, upper inner region 236 and lower inner region 234 may also be joined by a tapered region.

Figure 8:
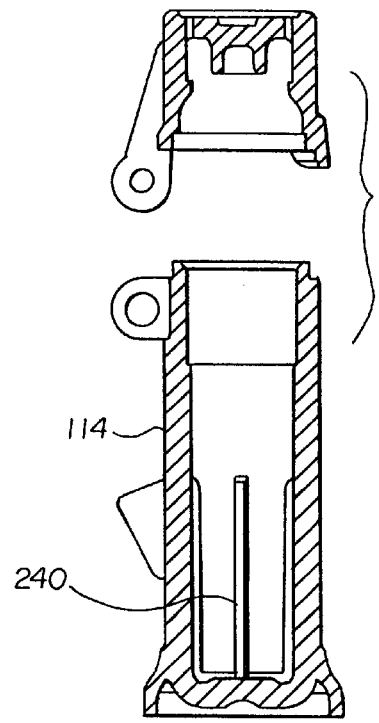
FIG. 8 shows side an elevational view of the elongated housing in cross-section.

Optional inner sleeve 194 is supported by one or more sleeve stop surfaces shown at 240 in FIG. 8 and disposed on the inner surface of elongated tubular housing 114. In a preferred embodiment, four or more sleeve support stop surface are present along the inner surface of elongated tubular housing 114.

Use of sleeves of different heights and/or internal configurations allows the package to be used with implants of different sizing and/or configurations.

Dental implant package 110 may further be provided with an optional base 258, as shown in FIG. 1, extending downward and/or outward from closed second end 122 of elongated tubular housing 114. Base 258 has a top 262 and a bottom 266 and is optionally chamfered from top 262 to bottom 266. Base 258 may be integrally formed with elongated tubular housing as one piece or may be fixedly attached to the bottom of the elongated tubular housing.

While a wide variety of materials are contemplated for the cap and elongated tubular housing, it is preferred that the cap and housing be formed of a transparent or nearly transparent material so that the practitioner can view at least a portion of the contents before opening the package. It is further desirable that the material be resistant to gamma radiation so that the package contents may be sterilized with gamma radiation at assembly. Suitable materials include treated polycarbonates such as Lexan™, Cycolac™, Valox™, Noryl™ and Ultem™. In a preferred embodiment, the cap and housing are made of HDPE (high density polyethylene) while the retainer is made of polystyrene.

The inner sleeve is preferably made of a biocompatible material such as titanium or an alloy thereof. It is desirable for the inner sleeve to be made of substantially the same material as the dental implant.

Figure 9:
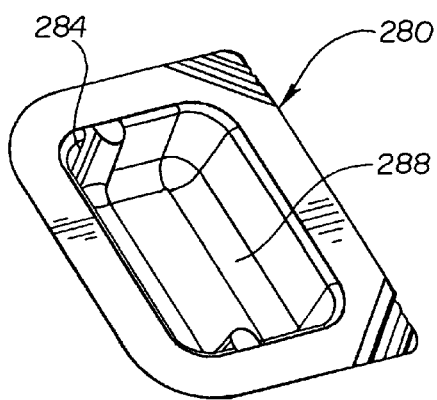
FIG. 9 shows a perspective view of an enclosure for holding the inventive packaging.
Figure 10:
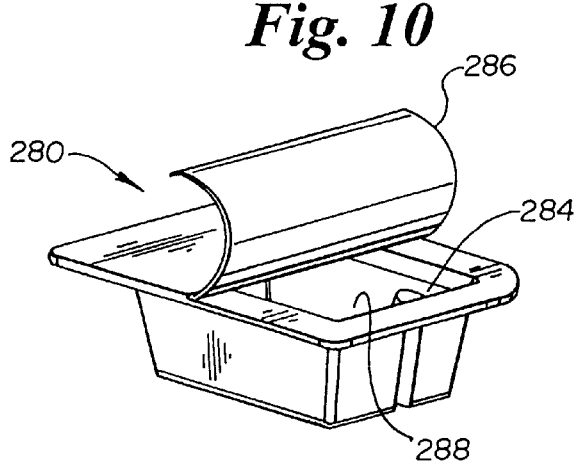
FIG. 10 shows the enclosure of FIG. 9 with the cover partially peeled away.

In FIGS. 9 and 10, the inventive dental implant package is carried within an enclosure, shown generally at 280, having a recess 288 therein for receiving the dental implant package. Adjacent to recess 288 is a second recess 284 into which additional material such as product literature may be inserted. Enclosure 280 further has a removable cover 286 for covering recess 284 and recess 288 when the dental implant package is disposed therein. Enclosure 280 is preferably made from a transparent or translucent material so that at least part of product literature contained within may be seen through the side of the enclosure. The removable cover may be made of a material such as Tyvek™.

The dental implant package may be furnished with a marking to indicate the size or type of the dental implant contained within. The cap may also be provided with a marking to indicate the size or type of the implant and healing screw contained within.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A dental implant package for supplying a dental implant and a healing screw at a surgical site when opened, the package comprising:
   an elongated tubular housing having a first end and a second end, an inner surface and an outer surface, the first end being open and the second end being closed, the elongated tubular housing having a length longer than the dental implant, the housing for receiving at least a portion of the dental implant; and
   a cap closing the first end of the elongated tubular housing, the cap having an interior surface and an exterior surface, the cap further comprising a retainer for the healing screw, the cap attached to the housing via a connector configured so that when the packages is opened, the healing screw and implant are presented in side-by-side relationship with the dental implant, the cap and elongated tubular housing further constructed and arranged so that the healing screw and dental implant are enclosed within the package when the cap is closed,
   whereby the implant and healing screw may be removed from the dental implant package without affecting the sterility of the implant and healing screw.

2. The dental implant package of claim 1 further comprising a removable inner sleeve resting within the elongated tubular housing and coaxial with the housing, the sleeve enclosing at least a part of the dental implant when the implant is present in the package, the sleeve having an inner diameter and an outer diameter.

3. The dental implant package of claim 2 further comprising one or more sleeve stop surfaces on the inner surface of the housing, the sleeve stop surfaces supporting the inner sleeve and preventing the removable inner sleeve from contacting the bottom of the housing.

4. The dental implant package of claim 2 wherein the inner sleeve has:
   an annular top and an annular bottom;
   an inner surface extending between the annular top and the annular bottom; and
   an outer surface extending between the annular top and the annular bottom, and wherein
   a portion of the annular top is chamfered inward toward the inner surface.

5. The dental implant package of claim 4 wherein a portion of the annular bottom is chamfered toward the outer surface.

6. The dental implant package of claim 4 wherein a portion of the annular bottom is chamfered inward toward the inner surface.

7. The dental implant package of claim 6 wherein the inner diameter of the sleeve is constant along the sleeve.

8. The dental implant package of claim 4 wherein the sleeve is further comprised of:
   an upper outer region having a uniform first outer diameter;
   a lower outer region having a uniform second outer diameter, the second outer diameter smaller than the first outer diameter;
   and a chamfered outer transition region extending between the first and second regions, the outer surface of the sleeve in the chamfered outer transition region chamfered downward from the upper outer region to the lower outer region.

9. The dental implant package of claim 8 wherein the inner diameter of the sleeve is constant along the sleeve.

10. The dental implant package of claim 9, the sleeve having a longitudinal axis therethrough, the longitudinal axis perpendicular to a horizontal reference plane, wherein the outer transition region is chamfered at an angle of about 45° relative to the horizontal reference plane.

11. The dental implant package of claim 8 wherein the sleeve is further comprised of:
    an upper inner region having a uniform first inner diameter;
    a lower inner region having a uniform second inner diameter, the second inner diameter smaller than the first inner diameter, the lower inner region adjacent to the upper inner region.

12. The dental implant package of claim 8, the sleeve having a longitudinal axis therethrough, the longitudinal axis perpendicular to a horizontal reference plane, wherein the outer transition region is chamfered at an angle of about 45° relative to the horizontal reference plane.

13. The dental implant package of claim 1 wherein the housing has an outer surface and the housing further comprises a support surface emanating from the outer surface of the housing, the support surface arranged so as to the provide support for the cap when the cap is fully opened and a downward force is applied to the cap when removing the healing screw contained therein.

14. The dental implant package of claim 1 wherein the retainer for the healing screw is substantially disk shaped.

15. The dental implant package of claim 1 wherein the cap is tubular and has a first end and a second end, the first end closed by a flat surface and the second end open, the inner tubular surface having a plurality of retainer stop surfaces, the retainer stop surfaces cooperating to retain the retainer for a healing screw.

16. The dental implant package of claim 15 wherein the retainer has a perimeter with notches cut therein so as to cooperate with the retainer stop surfaces on the inner tubular surface of the cap.

17. The dental implant package of claim 15 wherein the cap has four retainer stop surfaces.

18. The dental implant package of claim 1 wherein the retainer for a healing screw is arranged such that a bottom surface of the healing screw retained therein rests against the flat surface of the cap.

19. The dental implant package of claim 1, wherein the retainer has a hole through the center into which the healing screw is inserted, the diameter of the hole arranged so that the healing screw fits snugly therein.

20. The dental implant package of claim 19 wherein the retainer further comprises two perpendicular slots extending through the center of the retainer to grip the healing screw.

21. The dental implant package of claim 1 wherein the connector is a flexible piece of material attached at one end to the cap and attached at the other end to the housing.

22. The dental implant package of claim 1 wherein the connector comprises a first hinge element extending from the exterior surface of the cap and a second hinge element extending from the first end of the housing, the first and second hinge element cooperating so as to allow the housing to be opened at the first end.

23. The dental implant package of claim 1 further comprising a base extending from the bottom of the elongated tubular housing.

24. The dental implant package of claim 23 wherein
the base has a top and a bottom;
the base is integral with the elongated tubular housing; and
the base is chamfered outward from the top to the bottom.

25. The dental implant package of claim 23 wherein the base is fixedly attached to the bottom of the elongated tubular housing.

26. The dental implant package of claim 1 wherein the cap and housing are radiation transmissive.

27. The dental implant package of claim 1 wherein the cap and housing are formed of a material that is resistant to gamma radiation.

28. The dental implant package of claim 27 wherein the material is a treated polycarbonate or HDPE.

29. The dental implant package of claim 1 where the cap and housing are formed of a material that is transparent or translucent.

30. The dental implant package of claim 1 wherein the inner sleeve is made of a biocompatible material.

31. The dental implant package of claim 30 wherein the biocompatible material is titanium or an alloy thereof.

32. The dental implant package of claim 30 wherein the inner sleeve is made of substantially the same material as the dental implant.

33. In combination, a dental implant package as in claim 1 with a dental implant and a healing screw.

34. The combination of claim 33 wherein the dental implant package is closed and sterilized.

35. The combination of claim 34 further comprising an enclosure having a recess therein for receiving the dental implant package and a removable cover for covering the recess when the dental implant package is disposed therein.

36. A closed, sterilized dental implant package comprising:
an elongated capsule having a first end with an opening therein and a second end which is closed, the elongated capsule receiving at least a portion of the dental implant;
a cap for closing the first end of the capsule, the cap connected to the elongated capsule by a connector, the cap and the elongated capsule encompassing the dental implant and healing screw, the cap constructed and arranged to present the healing screw alongside the implant when the cap is fully opened, the cap further comprising a retainer for the healing screw;
an optional removable inner sleeve for holding the dental implant, the removable inner sleeve resting in the elongated capsule and supported by one or more optional stop surfaces therein; and
an optional base extending from the second end of the elongated capsule.

* * * * *